United States Patent [19]

von Gentzkow et al.

[11] Patent Number: 5,494,815

[45] Date of Patent: * Feb. 27, 1996

[54] IMMOBILIZATION OF BIOCHEMICAL SUBSTANCES ON A CARRIER CONTAINING A LAYER OF AN OLEFINIC-UNSATURATED, EPOXYFUNCTIONAL POLYSILOXANE

[76] Inventors: Wolfgang von Gentzkow, Zwetschgenweg 1, W 8524 Kleinsendelbach; Hans-Dieter Feucht, Eschenweg 7, W 7253 Renningen; Helmut Formanek, Römerhofweg 51, 8046 Garching; Gerhard Wanner, Rentamtstr. 9, 8052 Moosburg, all of Germany

[ * ] Notice: The portion of the term of this patent subsequent to Feb. 14, 2012, has been disclaimed.

[21] Appl. No.: 34,064

[22] Filed: Mar. 22, 1993

[30] Foreign Application Priority Data

Mar. 23, 1992 [DE] Germany .......................... 42 09 365.1

[51] Int. Cl.$^6$ .......................... C12N 11/00; C12N 11/14; G01N 33/551
[52] U.S. Cl. .......................... 435/174; 435/176; 435/179; 435/181; 436/524; 436/530; 436/532; 530/811; 530/814; 530/816
[58] Field of Search .......................... 435/174, 176, 435/177, 180, 181, 182, 179; 436/524, 530, 532; 530/811, 814, 816

[56] References Cited

U.S. PATENT DOCUMENTS

| | | | |
|---|---|---|---|
| 4,195,127 | 3/1980 | Hartdegen et al. | 435/174 |
| 4,547,431 | 10/1985 | Eckberg | 428/413 |
| 4,559,303 | 12/1985 | Aotani et al. | 435/180 |
| 5,024,942 | 6/1991 | Shimizu et al. | 435/134 |
| 5,080,936 | 1/1992 | Cerwen | 435/174 |

FOREIGN PATENT DOCUMENTS

| | | | |
|---|---|---|---|
| 160260A | 11/1985 | Germany . | |
| 291130A | 11/1988 | Italy . | |
| 0164953 | 9/1984 | Japan | 435/177 |

OTHER PUBLICATIONS

J. Microb. Biotechnol., vol. 6 (1991), pp. 44–57.
Hartmeier, W., "Immobilisierte Biokatalysatoren", Springer–Verlag Berlin, Heidelberg 1986, pp. 23–51.
W. Crueger and A. Crueger, "Biotechnologie—Lehrbuch der angewandten Mikrobiologie", R. Oldenbourg Verlag München, Wien 1989, pp. 201–203.
Woodward, J., "Immobilised cells and enzymes", IRL Press, Oxford, Washington, D.C. (1985), pp. 3–54.
S. A. Barker and I. Kay in "Handbook of Enzyme Biotechnology", (Editor: A. Wiseman), Ellis Horwood, Chichester 1975, Chapter 5, pp. 74–89.

Primary Examiner—David M. Naff
Assistant Examiner—Deborah K. Ware

[57] ABSTRACT

Biochemical substances, such as enzymes, are immobilized using an olefinic-unsaturated, epoxyfunctional polysiloxane. The polysiloxane is applied to a carrier material. The polysiloxane on the carrier is cross-linked by using high-energy radiation or a peroxide to form a polymer matrix. The polymer matrix is treated with an aqueous solution of a biochemical substance that reacts with epoxy groups and becomes immobilized. The polymer matrix is stabilized by the reaction of non-reacted epoxy groups with a compound containing an amino group, a carboxyl group or an amino group and a carboxyl group. The crosslinked polysiloxane can be hydrophilized after cross-linking and prior to immobilization of the biochemical substance by the reaction of a portion of the epoxy groups with a hydrophilic compound.

3 Claims, No Drawings

IMMOBILIZATION OF BIOCHEMICAL SUBSTANCES ON A CARRIER CONTAINING A LAYER OF AN OLEFINIC-UNSATURATED, EPOXYFUNCTIONAL POLYSILOXANE

FIELD OF THE INVENTION

The invention relates to a method for immobilization of biochemical substances, particularly enzymes.

BACKGROUND OF THE INVENTION

Because of their selectivity and high level of catalytic activity, enzymes are increasingly being used in many sectors of the food, pharmaceutical and chemical industries, for the production and analysis of products, as well as in medicine for diagnosis and therapy. Although enzymes are not used up in the conversion which they catalyze, they cannot be reused, because of their substrate solubility. This brings a number of disadvantages with it, and attempts have been made for quite some time to overcome these by using immobilized enzymes.

Immobilization is understood to be the transformation of water-soluble enzymes into a form insoluble in water, while maintaining their catalytic effectiveness. This is possible by chemical and/or physical binding of the water-soluble enzymes to a carrier insoluble in water, as well as by inclusion in gel matrices or microcapsules which are insoluble in water. The use of immobilized enzymes is limited, as a matter of principle, to processes with aqueous substrates or liquid substrates that contain water. The significant advantages of immobilized enzymes consist of the ease in separating them from the reaction solution and in the fact that they can be reused. These advantages result in significant cost savings, particularly in the case of enzymes which are not easily accessible and can be produced only in small yield. Since the end products remain free of enzymes, the heat treatment for inactivation of dissolved enzymes, which is necessary otherwise, is also eliminated, which is particularly advantageous in the case of heat-sensitive products. In addition, it is possible to use a continuous process with precise process control when using immobilized enzymes.

Every method with immobilized enzymes is in competition with the same method with dissolved enzymes. Immobilized enzymes are only competitive if clear economic advantages can be achieved with their use, for example in that improved and purer products are obtained, which can be processed more easily, faster and at a lower cost.

For the immobilization of enzymes, the following methods have been known:
adsorption
ionic binding
absorption
covalent binding to a carrier surface
inclusion in a matrix or in microcapsules
inclusion by sheathing with a membrane (macroencapsulation)
cross-linking or copolymerization with difunctional or polyfunctional monomers.

However, all of these methods are not universally applicable. Only when the application of an enzyme has been precisely defined can a suitable carrier, the immobilization method and the reactor form be selected and coordinated with one another (see, for example: W. Hartmeier, "Immobilisierte Biokatalysatoren" ["Immobilized Biocatalysts"], Springer-Verlag Berlin, Heidelberg 1986, pages 23 to 51, and J. Woodward, "Immobilised cells and enzymes", IRL Press, Oxford, Washington D.C., 1985, pages 3 to 54, as well as W. Crueger and A. Crueger, "Biotechnologie—Lehrbuch der angewandten Mikrobiologie ["Biotechnology—Handbook of Applied Microbiology"], R. Oldenbourg Verlag Munich, Vienna 1989, pages 201 to 203).

Physical adsorption of an enzyme on a carrier insoluble in water is the simplest and oldest method for immobilization of enzymes. It is based on non-specific physical interactions between the enzyme protein and the surface of the carrier material. The binding forces are mainly hydrogen bridges and van der Waals forces (see in this regard: S. A. Barker and I. Kay in "Handbook of Enzyme Biotechnology" (Editor: A. Wiseman), Ellis Horwood, Chichester 1975, Chapter 5, page 89). For immobilization, a concentrated enzyme solution is mixed with the carrier material carrier materials often used are activated charcoal, aluminum oxide, silicon dioxide, porous glass, cellulose and phenolic synthetic resins.

Adsorption has the disadvantage that because of the weak binding forces, desorption of the enzyme occurs over the period of use, by changes in temperature, pH or ionic strength, or due to the presence of other substances in the reaction solution. Another disadvantage is that adsorption is not specific, and thus further proteins or other substances can be adsorbed from the reaction solution. This can cause changes in the properties of the immobilized enzyme, and activity losses can occur.

In the case of ionic binding, the electrostatically charged enzyme molecule is attracted and fixed in place by a polyanionic or polycationic carrier with the opposite charge. As in the case of adsorption, again only a relatively weak bond occurs, since the charge of the enzyme protein is very small relative to its mass. The use of this method is also only possible for very low salt contents of the substrate solution, since other stronger ions can easily displace the enzyme molecules if they are present in the substrate. The ion exchanger resins which are most frequently used are DEAE cellulose (DEAE=diethylaminoethyl), DEAE Sephadex (an agarose preparation), and CM cellulose (CM=carboxymethyl). Also in the case of absorption in polymer layers, relatively unstable systems are obtained. Migration and extraction of the enzymes result in a constant decrease in activity and limit the lifetime of the enzyme layer.

Significantly more stable systems are achieved if the enzymes are covalently bound to a carrier surface, made insoluble via cross-linking or copolymerization, or are immobilized by microencapsulation or macroencapsulation. For the formation of covalent bonds and for cross-linking, free amino, carboxyl, hydroxyl and mercapto groups are available on the part of the enzymes. Both inorganic materials, such as glass, and natural and synthetic organic polymers can be used as the carrier material. A prerequisite in this connection is that the carrier materials contain reactive groups, such as isocyanate, isothiocyanate, acid chloride and epoxy groups. Less reactive groups can be activated, for example carboxyl groups can be activated using the carbodiimide or azide method, hydroxyl groups can be activated using the bromine cyan method, and amino groups can be activated using the isothiocyanate or azo method. It was possible, particularly on the basis of acrylic acid and methacrylic acid derivatives, to produce numerous reactive copolymers with dinitrofluorophenyl, isothiocyanate, oxirane or acid anhydride groups. Polyacrylamides with oxirane groups as well as modified copolymers on the basis of vinyl acetate and divinyl ethylene urea with oxirane groups are commercially available, for example.

Immobilization by cross-linking or by copolymerization represent special forms of covalent binding. In these methods, the formation of covalent bonds takes place between the enzyme molecules and difunctional or polyfunctional monomers, such as glutardialdehyde, or, in the case of copolymerization, additionally between the enzyme molecules and a polymerizing substance. In this manner, insoluble aggregates with a high molecular weight are formed. Cross-linking is generally used as an immobilization method in combination with one of the other methods, for example in combination with adsorption or absorption. Here, the enzyme molecules are first adsorbed on the surface of the carrier, or are absorbed in a layer located on it, and subsequently cross-linked.

A significant disadvantage of immobilization by covalent binding is the great stress on the biocatalysts connected with it. The immobilization procedures that are necessary, some of which are rough, in which a strong change in the pH occurs, organic solvents have to be used or reaction with reactive substances with a low molecular weight takes place, almost always lead to strong conformation changes and thus to activity losses of enzymes bound in such manner.

In immobilization by inclusion, i.e., microencapsulation or macroencapsulation, the enzymes themselves are not made insoluble, rather their reaction range is limited by semipermeable polymers or polymer layers. A prerequisite for the ability of enzymes sheathed in this manner to function is that substrates and products can pass through the sheathing substance, while the enzymes themselves have to be held back. In addition to natural polymers, such as alginate, carrageenan, pectin, agar and gelatin, which are, however, too large-meshed for permanent immobilization of enzymes, synthetic polymers, such as polyacrylamide, are particularly used for matrix sheathing. Polyamides, polyurethanes, polyesters and polyureas, for example, are used for encapsulation. The inclusion method has the disadvantage that relatively thick layers with long diffusion paths are formed.

SUMMARY OF THE INVENTION

It is an object of the invention to provide a method for immobilization of biochemical substances, which can be carried out in technically simple, low-loss, efficient and low-cost manner, and which yields immobilized enzymes with a stable function and sufficient catalytic activity, in a reproducible manner.

This is accomplished, according to the invention, by applying an olefinic-unsaturated, epoxyfunctional polysiloxane to a carrier material in the form of a layer. The polysiloxane is cross-linked to form a large-mesh epoxyfunctional polymer matrix by means of high-energy radiation or using peroxide. The layer is treated with an aqueous solution of the biochemical substance, whereby the biochemical substance is immobilized in the polymer matrix by reaction with epoxy groups. Finally, the layer is stabilized by reaction of non-converted epoxy groups with a compound containing amino and/or carboxyl groups.

DETAILED DESCRIPTION OF THE INVENTION

The invention provides a new method for immobilization of enzymes and other biochemical substances, specifically in cross-linked epoxyfunctional polysiloxanes. It was surprisingly found that these substances are able to penetrate into large-mesh cross-linked epoxyfunctional polysiloxanes—from aqueous solution—and can be anchored in the polymer matrix, i.e. in the polymer network, under very mild conditions, by reaction with epoxy groups in chain position. This fact is completely new, and it opens up the possibility of very gentle immobilization. The method according to the invention is not limited to the immobilization of enzymes, but rather also allows for the immobilization of other biochemical substances, such as coenzymes, enzyme inhibitors, effectors and antibodies.

The method according to the invention includes the following steps, in general:

1. Coating of carrier materials

An epoxyfunctional polysiloxane which can be cross-linked by radicals, or a mixture of such polysiloxanes is applied, in the desired layer thickness, to a carrier material, if necessary in combination with a cross-linking initiator, a cross-linking reinforcer and/or other additives. The carrier can consist of inorganic or organic material and be present in the form of fibers, non-woven material, paper or woven material, or in the form of planar materials. The use of porous or pore-free membrane materials can prove to be particularly advantageous. Depending on the application case and the flow behavior of the polysiloxane used, coating can be carried out using a solution or without solvent, by dipping, spin-coating, roller-coating, curtain-coating or another conventional technical process, where it might be necessary to pretreat the carrier surface with an adhesion agent. In the case of material which extends lengthwise, continuous coating can take place. The layer thickness can be controlled by adjusting the viscosity and by adding a solvent or a reactive diluent. The layer produced in this manner must be freed of volatile components, in every case, which can be done by drying or degassing, for example. To improve the adhesion of the coating on the carrier surface, which has been treated with an adhesion agent, if necessary, a tempering step can prove to be advantageous.

2. Cross-linking of the coating

Cross-linking of the coating, i.e., the polysiloxane, takes place by means of high-energy radiation, particularly UV, electron or $\gamma$ radiation, or with peroxide. For cross-linking with peroxide, organic peroxides are brought into the polysiloxane or into the polysiloxane mixture. Cross-linking is initiated by thermal decomposition of the peroxides to form radicals. Heat transfer to the coating can take place by means of IR radiation, microwaves, heated rolling or pressing tools, or by means of hot gases. As a result of the cross-linking, during which only the olefinic-unsaturated groups that can be polymerized by radicals are converted, while the epoxy groups are quantitatively maintained, a large-mesh polymer network is formed.

3. Immobilization of the biochemical substance

Upon contacting of the cross-linked layer with an aqueous solution of the biochemical substance, this substance migrates into the polymer matrix and is covalently bound there by reaction with the epoxy groups. A prerequisite for this process, along with the necessary mesh width, is sufficient hydrophilicity of the polymer network formed during cross-linking. Immobilization can therefore be accelerated by prior hydrophilization of the polysiloxane. This is done by conversion of part of the epoxy groups with hydrophilic compounds which contain reactive groups, such as NH, OH, SH or COOH groups, causing the hydrophilic character of the polymer layer to be increased. The immobilization process can also be significantly accelerated by means of additives, such as polyvinyl pyrrolidone, which result in increased water absorption of the polysiloxanes, as well as by solvents which are miscible with water, such as dioxane, tetrahydrofuran, alcohols or polyethers. Furthermore, several different biochemical substances can also be immobilized in a single layer, and this can be done either simultaneously or consecutively.

4. Stabilization of the coating

This step includes the reaction of epoxy groups remaining after immobilization, with a compound containing amino and/or carboxyl groups, particularly an amino acid. Depending on the compound used, stabilization can be utilized to achieve closer cross-linking of the layer, and thus improved mechanical strength, or for adaptation of the material properties and the material transport. Furthermore, a superficial covering of this layer with one or more additional layers is possible, which might also be practical for adjusting defined diffusion conditions of the reaction partners and products to be converted.

For the method according to the invention, epoxyfunctional polysiloxanes with the following structure are particularly suitable; these are the subject of the U.S. patent application Ser. No. 08/034,063—"Polysiloxanes" filed on the same day as this application:

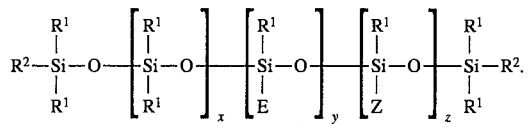

Here, the following applies:

E=epoxyfunctional remainder with 4° to 20° C. atoms,

Z=vinyl group or photopolymerizable remainder with 8° to 40° C. atoms, which can be obtained by addition of a photopolymerizable compound to a remainder E located at the siloxane chain, and subsequent addition of an aliphatic, cycloaliphatic or aromatic monoisocyanate or monoisothiocyanate with 2° to 10° C. atoms to the secondary OH group formed upon opening of the epoxide ring, $R^1$=alkyl with 1° to 4° C. atoms or phenyl, $R^2$=$R^1$, E or Z, where the remainders $R^1$ and $R^2$ can be the same or different in each instance, x=50 to 1000, y=10 to 300, z=3 to 8;

x is preferably about 3 to 10 times y. In the formula, the individual structural groups of the polysiloxanes are indicated in summary form; in fact, these groups are statistically distributed over the polymer chain.

The epoxyfunctional remainder E is preferably one of the following remainders:

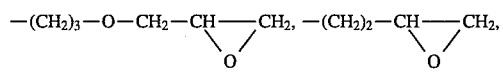

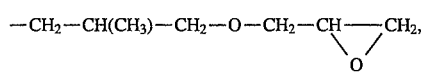

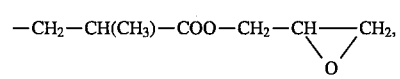

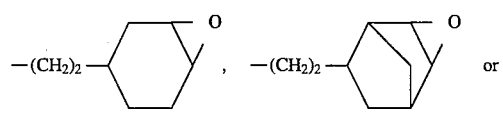

-continued

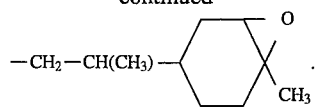

Photopolymerizable compounds, i.e., olefin-unsaturated compounds which are suitable for the reaction with epoxy groups i.e. with the remainder E, are acrylic acid, methacrylic acid, hydroxyethyl acrylate, hydroxyethyl methacrylate, hydroxyethyl maleinimide, cinnamic acid, glycerol diacrylate and glycerol dimethacrylate. A suitable monoisocyanate is propyl isocyanate, for example.

Polysiloxanes of the type stated above which have vinyl groups are known from EP-OS 0 336 854.

The epoxyfunctional polysiloxanes used in the invention are produced by reacting polysiloxanes having epoxy groups with an olefinic-unsaturated compound containing hydroxyl or carboxyl groups in a molar ratio of <1, with reference to the epoxy groups, and adding a monoisocyanate or monoisothiocyanate on the hydroxyl groups formed in this way.

The polysiloxanes with epoxy groups can be obtained by addition of epoxy compounds with an ω positioned C=C double bond to SiH-functional polysiloxanes. Suitable epoxy compounds are particularly allyl glycidyl ether, 2-methyl-allyl glycidyl ether, epoxy butene, methacrylic acid glycidyl ester, vinyl cyclohexene oxide, vinyl norbornene oxide and limonene oxide. The same or very similar polysiloxanes are also accessible by epoxidation of polysiloxanes with chain-positioned ω-alkenyl, ω-alkenyl ether and ω-alkenyl ester groups.

Olefinic-unsaturated compounds which are particularly suitable for the reaction with the epoxy groups of the polysiloxanes produced in the manner stated are acrylic acid, methacrylic acid, hydroxyethyl acrylate, hydroxyethyl methacrylate, hydroxyethyl maleinimide, cinnamic acid, glycerol diacrylate and glycerol dimethacrylate, or mixtures of these compounds. Acrylic acid and methacrylic acid, in particular, can also find use in a mixture with the corresponding anhydrides. The compounds according to the invention are obtained by reaction of the products formed by the addition of the olefinic-unsaturated compounds to the polysiloxanes which have epoxy groups, with monoisocyanate or monoisothiocyanate. In this reaction, the iso(thio)cyanates react with the vicinal hydroxyl group, which is formed by opening of the oxirane ring during the previous addition reaction. Preferably, propyl isocyanate is used as the monoisocyanate. Other possible compounds are, for example butyl isocyanate and phenyl isocyanate as well as propyl isothiocyanate and phenyl isothiocyanate.

The method according to the invention offers the following advantages:

It allows immobilization of all biochemical substances which have reactive NH, OH, SH or COOH groups at their periphery.

Layers produced according to this method, with immobilized biochemical substances, can also be stored dry and under non-sterile conditions, without any damage to these substances.

Immobilization of the biochemical substances takes place under very mild conditions, in aqueous solution and in the absence of reactive components with a low molecular weight; in this way losses, for example as a result of enzyme denaturing, are avoided.

A relatively small number of polymer materials with great chemical and thermal stability, which can be produced on a large technical scale and which are therefore accessible at low cost, is used for immobilization of a large number of different types of biochemical substances.

The production and cross-linking of the layers can be carried out in technically simple, reproducible and low-cost manner. When using goods which run to length as the carrier, such as films, textiles, hoses and strips, continuous methods of operation can be used.

Immobilization of the biochemical substances can take place independent of the layer production, depending on the need and intended use, if necessary not until just before use, to be carried out by the user.

Desorption, migration and extraction losses are avoided by chemical anchoring of the biochemical substances in the polymer matrix.

By the formation of covalent bonds between the peripheral NH, OH, SH and COOH groups of the biochemical substances and the very soft and flexible sheathing polymer material, the substances, some of which are very sensitive, for example enzymes, are given great functional and long-term stability.

The production of very thin layers (<<1 μm) allows very short diffusion paths for reaction partners and products.

Since size, shape, hydrophilicity and reactivity of the biochemical substances to be immobilized play a large role in the method according to the invention, the immobilization is connected with a certain selection and cleaning; this allows for the use of low-cost products with low activity in many cases.

The method according to the invention can be used technically anywhere where immobilized biochemical substances are already in use today, or where they could be advantageously used. This method offers particular advantages for use in enzyme reactors, such as those used on a technical scale for the production of L-amino acids from acetyl-DL-amino acids, α-ketone-carboxylic acids, α-hydroxycarboxylic acids or α,β-unsaturated carboxylic acids, for the production of L-malic acid from fumaric acid, for isomerization of glucose as well as for penicillin derivatization. In this connection, the immobilization of the enzymes required can take place in thin layers, on very different materials. Aside from various metals and metal oxides, a large number of different plastics are also possible materials. Immobilization in layers on porous membranes offers special advantages for use in membrane reactors.

Use of the method according to the invention also brings advantages in the identification, separation and cleaning of biochemical materials. In analysis, use within the scope of affinity chromatography, in particular, offers interesting application possibilities. In medicine, the method according to the invention can be used for intracorporeal and extracorporeal enzyme therapy and for the production of artificial organs, for example artificial kidneys. By immobilization of certain biochemical substances, such as heparin, the biocompatibility of the polysiloxane layers can be increased, so that these can serve as the coating for implants, for example.

The invention will be explained in more detail with reference to the following examples which are illustrative of the invention.

EXAMPLE 1 TO 5

Synthesis of Polysiloxanes Containing Epoxy Groups (Polyepoxysiloxanes) as the Starting Compounds for the Production of the Epoxyfunctional Polysiloxanes used in the Invention, Which Can Be Photo-cross-linked

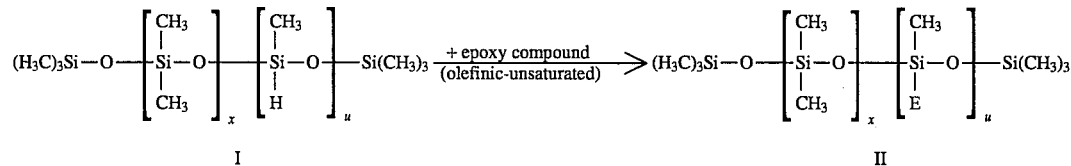

The mass parts of octamethyl cyclotetrasiloxane (OMCTS), SiH-functional polymethyl siloxane with a chain length of n=60 (PMS) and hexamethyl disiloxane (HMDS) as indicated in Table 1 are mixed with 0.2 g trifluoromethane sulfonic acid and 13 drops of distilled water, and stirred at 70° C. for 40 h. After cooling, the reaction mixture is mixed with approximately 1 g $Na_2CO_3$, stirred for 2 h and filtered through a membrane filter with a pore diameter of 1.2 μm under pressure. Volatile constituents are first removed at 100° C./0.1 mbar, and then in a thin-layer evaporator at 120° C./0.1 mbar.

The colorless liquid obtained is dripped into a solution of the amount of freshly distilled epoxide indicated in Table 1, i.e., allyl glycidyl ether (AGE), vinyl cyclohexene oxide (VCHO) or limonene oxide (LO), 0.13 g $H_2PtCl_6.6 H_2O$ and 0.5 ml tert.-butanol in 250 ml toluene, at 70° C., within 6 to 7 h. The reaction mixture is then stirred at 70° C. until a minimum conversion of 95% has been reached (verification by volumetric determination of SiH). To remove the catalyst, 0.2 g cross-linked poly-4-vinyl pyridine is added, then the mixture is stirred at room temperature for 2 h, and filtered under pressure through a membrane filter with a pore diameter of 1.2 μm. The solvent as well as volatile constituents are removed in a vacuum at 70° C./0.1 mbar. Colorless liquids are obtained in almost quantitative yield. Table 1 contains the epoxy values and viscosities determined for characterization of the products.

TABLE 1

| | Reaction Components (mass data in g) | | | | | | Polyepoxysiloxane II (chain length n = x + u) | | | Epoxy Value | Viscosity |
|---|---|---|---|---|---|---|---|---|---|---|---|
| No. | OMCTS | PMS | HMDS | AGE | VCHO | LO | n | x | u | [mol/100 g] | [mPa · s] |
| 1 | 297 | 61 | 5.4 | 142.4 | — | — | 100 | 80 | 20 | 0.21 | 520 |
| 2 | 297 | 61 | 2.7 | 142.8 | — | — | 150 | 120 | 30 | 0.21 | 540 |
| 3 | 297 | 61 | — | 143.2 | — | — | 300 | 240 | 60 | 0.21 | 870 |
| 4 | 297 | 61 | 2.7 | — | 152.4 | — | 150 | 120 | 30 | 0.21 | 550 |
| 5 | 297 | 61 | 2.7 | — | — | 189.8 | 150 | 120 | 30 | 0.19 | 560 |

EXAMPLES 6 to 8

Reaction of compound II of Examples 1 to 5 with acrylic acid (AS) or methacrylic acid (MAS) to produce olefinic-unsaturated, epoxyfunctional polysiloxanes

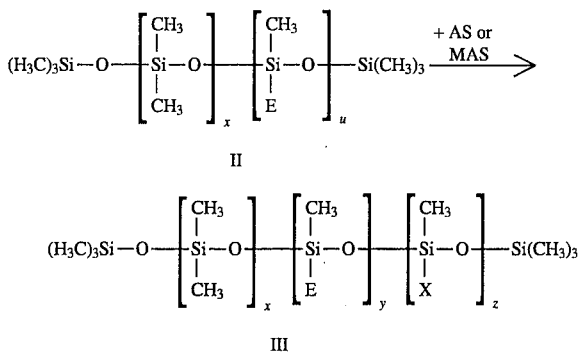

The mass parts of the products 1 and 2 given in Table 2 are dissolved in 500 ml water-free toluene under yellow light, with the mass parts of acrylic acid (AS) or methacrylic acid (MAS) also indicated in Table 2, together with 2.5 g diethyl phosphite as the stabilizer and 2.5 g N,N,N',N'-tetramethyl-4,4'-diamino diphenyl methane as the catalyst, then stirred at 50° C. for 10 to 11 h. After cooling, the reaction mixture is mixed with acid $Al_2O_3$ to remove the catalyst, stirred for 2 h and pressure-filtered through a membrane filter with a pore diameter of 1.2 μm. The solvent and volatile constituents are removed at room temperature, in a vacuum (0.1 mbar). The products obtained are unstable and already gel during further processing or when stored in the refrigerator.

EXAMPLES 9 to 16

Production of the Epoxyfunctional Polysiloxanes According to the Invention, Which Can be Photo-cross-linked

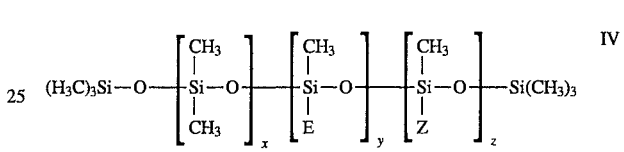

The mass parts of the products 1 to 5 indicated in Table 3 are reacted in toluene, as described in Examples 6 to 8, with acrylic acid or methacrylic acid, 2.5 g diethyl phosphite and 2.5 g N,N,N',N'-tetramethyl-4,4'-diamino diphenyl methane. However, the solution is not concentrated after the catalyst has been removed, but rather mixed with 14.2 g propyl isocyanate and 20 drops of dibutyl tin dilaurate, and stirred at room temperature for 120 h. Then, excess isocyanate is inactivated by adding a few drops of methanol, and then the solvent as well as volatile constituents are removed at room temperature, in a vacuum (0.1 mbar). Colorless clear liquids are obtained in yields between 90 and 100%. Further information relating to the products obtained (epoxy value, acrylate content, viscosity) is summarized in Table 4.

The products must be stored in the refrigerator. An evaluation of the storage stability by weekly determinations of viscosity, which is allowed to increase by a maximum of 5%, yields values of >3 months.

TABLE 2

| | Reaction Components (mass data in g) | | | | Polyepoxysiloxane III (chain length n = x + y + z) | | | | Epoxy value | |
|---|---|---|---|---|---|---|---|---|---|---|
| | Polyepoxysiloxane II | | | | | | | | | |
| No. | 1 | 2 | AS | MAS | n | x | y | z | [mol/100 g] | Comment |
| 6 | 477.3 | — | — | 17.3 | 100 | 80 | 16 | 4 | 0.16 | gelling when stored in refrigerator |
| 7 | — | 475 | — | 14.3 | 150 | 120 | 25 | 5 | not determinable | gelling when processed |
| 8 | — | 475 | 12.0 | — | 150 | 120 | 25 | 5 | not determinable | gelling when processed |

TABLE 3

| | Reaction Components (mass data in g) | | | | | | | | | | |
|---|---|---|---|---|---|---|---|---|---|---|---|
| | Polyepoxysiloxane II | | | | | | | Polyepoxysiloxane IV (chain length n = x + y + z) | | | |
| No. | 1 | 2 | 3 | 4 | 5 | AS | MAS | n | x | y | z |
| 9 | 477.3 | — | — | — | — | — | 17.3 | 100 | 80 | 16 | 4 |
| 10 | — | 475 | — | — | — | — | 14.3 | 150 | 120 | 25 | 5 |
| 11 | — | 475 | — | — | — | 12.0 | — | 150 | 120 | 25 | 5 |
| 12 | — | — | 472.6 | — | — | — | 11.4 | 300 | 240 | 52 | 8 |
| 13 | — | — | 472.6 | — | — | — | 8.5 | 300 | 240 | 54 | 8 |
| 14 | — | — | 472.6 | — | — | — | 5.6 | 300 | 240 | 56 | 4 |
| 15 | — | — | — | 482.6 | — | — | 14.5 | 150 | 120 | 25 | 5 |
| 16 | — | — | — | — | 512.5 | 16.8 | — | 150 | 120 | 23 | 7 |

TABLE 4

| | Polysiloxane IV which can be photo-cross-linked | | |
|---|---|---|---|
| No. | Epoxide [mol/100 g] | Acrylate [mol/100 g] | Viscosity [mPa · s] |
| 9 | 0.16 | 0.04 | 2200 |
| 10 | 0.17 | 0.03 | 2400 |
| 11 | 0.17 | 0.03 | 2380 |
| 12 | 0.18 | 0.03 | 3000 |
| 13 | 0.19 | 0.02 | 2850 |
| 14 | 0.20 | 0.01 | 2800 |
| 15 | 0.16 | 0.03 | 2400 |
| 16 | 0.14 | 0.04 | 2500 |

EXAMPLE 17

Production of Polysiloxane/Enzyme Layers 100 parts by mass of an epoxyfunctional polysiloxane with the structure

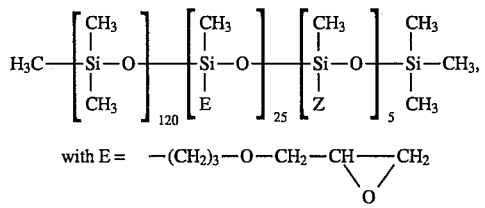

with E = $-(CH_2)_3-O-CH_2-CH\underset{O}{\overset{\diagdown\;\diagup}{-}}CH_2$ and

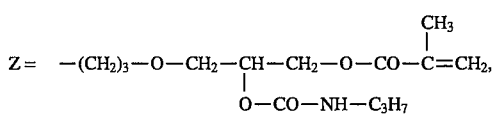

are mixed with 7 parts by mass propoxylated glycerol triacrylate as the reactive diluent and 2 parts by mass 2-hydroxy-2-methyl-1-phenyl propan-1-one as the photoinitiator, and mixed with a corresponding amount of toluene to adjust the desired processing properties. This solution is then applied to the surface of the carrier material, which has been pretreated with an adhesion agent, if necessary, by dipping, dripping or spreading. Parallel to this, silicon wafers are coated with the same solution, using a varnish centrifuge; the centrifuge time is approximately 10 s.

The layers are dried in a laminar box and subsequently cross-linked under nitrogen, by UV irradiation (System F 450 of the company Fusion UV-Curing Systems) in a wavelength range of 200 to 450 nm; irradiation period: 3.2 s. To remove soluble components, the cross-linked layers are extracted with dioxane for 24 h, at room temperature. To increase the hydrophilicity of the layers, part of the epoxy groups is reacted with compounds containing NH groups, in the form of amino acids. In this connection, storage of the layers in a 2% solution of proline or glutaminic acid in a 2:1 mixture of dioxane and water at 40° to 60° C. has particularly proven to be effective. Using silicon wafers treated in a corresponding manner, the conversion can be followed by IR spectroscopy. A conversion of 50% is sufficient in most cases; if needed, however, higher values can also be adjusted.

Immobilization of the enzymes takes place by incubation of the layers in an approximately 1 to 2% solution of the enzyme in water at 20° to 30° C. To accelerate this process, the solution can be mixed with 10 to 50% dioxane, depending on the sensitivity of the enzyme. Immobilization is complete after 1 to 8 h. Remaining epoxy groups can be eliminated by gentle conversion with amino acids. As the last step, the layers are freed from extractable components by being intensively washed with water.

Table 5 contains a summary of the enzymes immobilized according to the invention, in identically pretreated layers with a thickness of 10 μm, on silicon wafers, immobilized at 30° C. within 4 h, as well as the enzyme activity at 25° C.

EXAMPLE 18

Influence of the Enzyme Activity on the Activity of Polysiloxane/Enzyme Layers

A polysiloxane layer produced on a filter paper according to Example 17, with a thickness of approximately 20 μm, is incubated for 6 h at 60° C., in a 2% solution of proline in a 2:1 mixture of dioxane and water, after UV cross-linking and extraction with dioxane. The filter paper is divided, and the one half if treated with a 2% aqueous solution of glucose oxidase with an activity of 22 U/mg, and the other half is treated with a 2% aqueous solution of glucose oxidase with an activity of 276 U/mg, each for 8 h at 30° C. Both halves are then watered separately for 24 h. Subsequently, samples with a size of 1 cm$^2$ of the two halves are examined for activity by means of the Gluc-DH method. For the first half, a mean activity of 2.0 U/cm$^2$ is determined, while for the second half, a mean activity of 2.2 U/cm$^2$ is determined. This result shows that the activity of the polysiloxane/enzyme layers is practically independent of the activity of the enzyme used.

TABLE 5

| Enzyme | Activity | Determination Method |
| --- | --- | --- |
| Glucose oxidase from *Aspergillus niger*, lyophil. 240 U/mg | 1.2 U/cm² | Gluc-DH Method of the Merck company |
| Catalase from cattle liver, suspension 65,000 U/mg | 550 U/cm² | See: B. Stellmach, "Determination Methods for Enzymes", Steinkopff-Verlag, Darmstadt 1988, pages 152 to 155 |
| Urease from broad beans, lyophil. 100 U/mg | 1.0 U/cm² | See: B. Stellmach, "Determination Methods for Enzyme", Steinkopff-Verlag, Darmstadt 1988, pages 269 to 271 |
| Alcohol dehydrogenase from yeast, lyophil. 400 U/mg | 3.2 U/cm² | See: B. Stellmach, "Determination Methods for Enzymes", Steinkopff-Verlag Darmstadt 1988, pages 11 and 12 |
| L-asparaginase, 50% solution in glycerol 80 U/mg solution | 0.8 U/cm² | See: B. Stellmach, "Determination Methods for Enzyme", Steinkopff-Verlag, Darmstadt 1988, pages 63 to 68 |

EXAMPLE 19

Production of Polysiloxane Layers for Immobilization of Enzymes on Various Carrier Materials The mixture of epoxyfunctional polysiloxane, reactive diluent and photoinitiator described in Example 17 is dissolved in different amounts of toluene. The solutions obtained are applied to different carrier materials, described in greater detail in Table 6, by means of dipping (=D) or spin-coating (=S). Solid materials are first polished and cleaned on their surface, and coated by means of spin-coating, if necessary after pretreatment with an adhesion agent; the centrifuge time is 10 s. Films, membranes and non-wovens are either glued onto a solid carrier and coated by means of spin-coating or dipped. Woven textiles are coated by means of dipping and subsequently stripping or pressing the excess polysiloxane off. All layers are crosslinked by means of UV-radiation, as described in Example 17.

Table 6 contains a summary of the materials and coating techniques used, as well as the polysiloxane layer thicknesses. The adhesion of the layers to the carrier material was determined by 24-hour storage and swelling in dioxane. The layers can be utilized for immobilization of enzymes, as described in Example 17.

TABLE 6

| Carrier material (* = in wafer form) | Adhesion agent | Coating technique | Layer thickness (μm) | Adhesion |
| --- | --- | --- | --- | --- |
| Silicon* | − | S | 0.1–30 | − |
|  | + | S | 0.1–30 | + |
| Quartz* | − | S | 0.1–30 | − |
|  | + | S | 0.1–30 | + |
| Epoxy resin* | − | S | 0.1–30 | + |
|  | + | S | 0.1–30 | + |
| Polyether etherkeytone* | − | S | 0.1–30 | + |
| Polysiloxane layer | − | S | 0.1–30 | + |

TABLE 6-continued

| Carrier material (* = in wafer form) | Adhesion agent | Coating technique | Layer thickness (μm) | Adhesion |
| --- | --- | --- | --- | --- |
| on silicon* |  |  |  |  |
| Polyester membrane | − | S | 0.1–30 | + |
| Cellulose membrane | − | S | 0.1–30 | + |
| Cellulose filter paper | − | D | 50–150 | + |
| Acetyl cellulose membrane | − | S | 0.1–30 | + |
| Nylon 6,6 woven textile | − | D | 100–150 | + |
| Fiberglass woven textile | − | D | 100–200 | + |

EXAMPLE 20

Evaluation of the Effectiveness of Polysiloxane/Enzyme Layers

Analogous to Example 19, a layer of the polysiloxane described in Example 17, with a thickness of approximately 6 μm, is produced on a polyester membrane with a layer thickness of 14 μm, by means of spin-coating. Corresponding to Example 17, this composite is treated with proline for 6 h at 60° C., and is then treated for 6 h at 30° C. with an aqueous enzyme solution. The following enzymes are immobilized: fumarase, activity 200 U/mg; L-aspartase, activity 5 U/mg.

Fumarase catalyzes the conversion of fumaric acid with water to L-malic acid. L-aspartase catalyzes the conversion of fumaric acid with ammonia to L-asparginic acid. Since both enzymes also catalyze the reverse reaction in each case, an excess of initial components is used. The conversion in the presence of fumarase takes place at a pH of 7.5, while the conversion in the presence of L-aspartase takes place at a pH of 8.5. The decrease in fumaric acid concentration is determined by iodometry (see in this regard: "Chem. Ber." ["Chemical Reports"], Vol. 70 (1937), pages 903 to 907).

The two conversions are carried out in such a manner that the one time, approximately 10 cm² of the membrane containing aspartase is placed in 200 ml of a solution of 2% fumaric acid and 2% ammonia (NH₄OH), and the other time, approximately 1 cm² of the membrane containing fumarase is placed in 400 ml of a solution of 2% fumaric acid, and the solutions are stirred. In order to avoid strong changes in concentration, the reaction is interrupted after 24 h in each case, the fumaric acid concentration is determined and the reaction solution is replaced with a freshly prepared solution.

The conversion curves determined show that the activity of the two enzymes is practically not reduced over a period of 5 days.

What is claimed is:

1. A method for immobilization of a biochemical substance having an amino, hydroxyl, mercapto or carboxyl functional group, comprising the steps of:

applying an olefinic-unsaturated, epoxyfunctional polysiloxane to a carrier material in the form of a layer, wherein the polysiloxane has the structure:

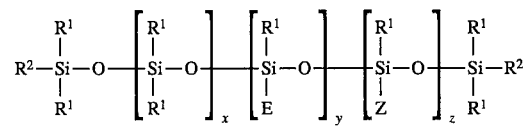

where the following applies:

E=an epoxyfunctional remainder with 4° to 20° C. atoms, selected from the group consisting of:

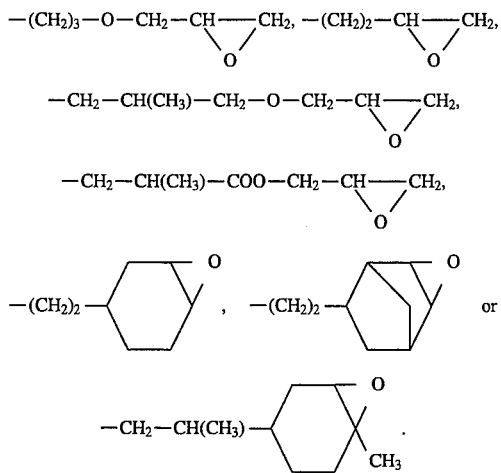

Z=a vinyl group or photopolymerizable remainder with 8° to 40° C. atoms, which is obtained by addition of a photopolymerizable compound to a remainder E located at the siloxane chain, and subsequent addition of an aliphatic, cycloaliphatic or aromatic monoisocyanate or monoisothiocyanate with 2° to 10° C. atoms to the secondary OH group formed upon opening of the epoxide ring, $R^1$=alkyl with 1° to 4° C. atoms or phenyl, $R^2=R^1$, E or Z, where the remainders $R^1$ and $R^2$ can be the same or different in each instance, x=50 to 1000, y=10 to 300, z=3 to 8, cross-linking the polysiloxane by means of high-energy radiation or using peroxide, to form an epoxyfunctional polymer matrix, treating the polymer matrix with an aqueous solution of the biochemical substance, whereby the biochemical substance is immobilized in the polymer matrix by reaction with epoxy groups, and stabilizing the polymer matrix by reaction of non-reacted epoxy groups with a compound containing an amino group, a carboxyl group or an amino group and a carboxyl group.

2. The method according to claim 1 further comprising the step of hydrophilizing the cross-linked polysiloxane after cross-linking and prior to immobilization of the biochemical substance by reaction of a portion of the epoxy groups with a hydrophilic compound.

3. The method according to claim 1 wherein the biochemical substance is an enzyme.

* * * * *